United States Patent
Niggl et al.

(10) Patent No.: US 9,778,106 B2
(45) Date of Patent: Oct. 3, 2017

(54) SPECTROMETER WITH MONOCHROMATOR AND ORDER SORTING FILTER

(71) Applicant: TECAN Trading AG, Männedorf (CH)

(72) Inventors: Lutz Niggl, Waging (DE); Andreas Erlbacher, Grodig (AT); Frank Münchow, Freilassing (DE)

(73) Assignee: TECAN TRADING AG, Männedorf (CH)

(*) Notice: Subject to any disclaimer, the term of this patent is extended or adjusted under 35 U.S.C. 154(b) by 88 days.

(21) Appl. No.: 14/794,316

(22) Filed: Jul. 8, 2015

(65) Prior Publication Data

US 2016/0011048 A1    Jan. 14, 2016

(30) Foreign Application Priority Data

Jul. 11, 2014 (CH) .................................. 01054/14

(51) Int. Cl.
*G01J 3/18* (2006.01)
*G01J 3/06* (2006.01)
(Continued)

(52) U.S. Cl.
CPC . *G01J 3/18* (2013.01); *G01J 3/06* (2013.01); *G01J 3/42* (2013.01); *G01N 21/253* (2013.01); *G01N 21/31* (2013.01); *G01N 35/028* (2013.01); *G01J 2003/1204* (2013.01); *G01J 2003/1213* (2013.01); *G01J 2003/1217* (2013.01); *G01N 2021/3174* (2013.01); *G01N 2201/084* (2013.01)

(58) Field of Classification Search
CPC .................. G01J 2003/1273; G01J 2003/1828
See application file for complete search history.

(56) References Cited

U.S. PATENT DOCUMENTS

| 3,711,708 A | 1/1973 | Geiger et al. | |
| 4,264,205 A * | 4/1981 | Landa | G01J 3/02 356/326 |

(Continued)

FOREIGN PATENT DOCUMENTS

| EP | 0015607 A1 | 9/1980 |
| WO | 93/22636 A1 | 11/1993 |

OTHER PUBLICATIONS

European Search Report for Application No. EP15172759 filed Jun. 18, 2015.

*Primary Examiner* — Shawn Decenzo
(74) *Attorney, Agent, or Firm* — Notaro, Michalos & Zaccaria P.C.

(57) ABSTRACT

A spectrometer (1) comprises a light source (2), a monochromator (3) with at least one diffraction grating (4), a monochromator housing (5), an order sorting filter (7), a microplate receptacle (12) and a controller (6). The order sorting filter (7) of the spectrometer (1) comprises a substrate (23), a first optical thin film (24) and a second optical thin film (25), wherein, in a spatially partly overlapping and interference-free manner, the first optical thin film (24) is arranged on a first surface (26) and the second optical thin film (25) is arranged on a second surface (27) of the substrate (23). A spectrometer (1) equipped with a respective order sorting filter is used in a scanning method for detecting the absorption spectrum of samples examined in wells (14) of microplates (13).

22 Claims, 4 Drawing Sheets

(51) Int. Cl.
  *G01J 3/42*   (2006.01)
  *G01N 35/02*  (2006.01)
  *G01N 21/25*  (2006.01)
  *G01N 21/31*  (2006.01)
  *G01J 3/12*   (2006.01)

(56) References Cited

U.S. PATENT DOCUMENTS

| | | | | |
|---|---|---|---|---|
| 5,139,335 A | * | 8/1992 | Lundeen | G01J 3/1838 356/328 |
| 6,313,471 B1 | * | 11/2001 | Giebeler | G01N 21/6452 250/458.1 |
| 6,809,859 B2 | * | 10/2004 | Erdogan | G02B 5/285 359/359 |
| 7,924,422 B2 | * | 4/2011 | Stanke | G01J 3/02 356/326 |
| 2004/0207815 A1 | * | 10/2004 | Allen | G09G 3/007 353/31 |
| 2005/0031499 A1 | * | 2/2005 | Meier | B06B 3/00 422/128 |
| 2009/0168182 A1 | * | 7/2009 | Chang | G02B 5/285 359/589 |

* cited by examiner

SPECTROMETER WITH MONOCHROMATOR AND ORDER SORTING FILTER

BACKGROUND OF THE INVENTION

Field of the Invention

The invention relates to a spectrometer with monochromator and order sorting filter for absorption spectrometry on samples in microplate wells, as well as a scanning method for detecting the absorption spectrum of samples in microplate wells, in which a spectrometer equipped with a monochromator and such an order sorting filter is used.

Spectrometers with monochromator have been known for a longer period of time and are used for example for generating illumination light of a specific wavelength for the examination of the absorption characteristics of clear low-molecular solutions. Spectrometers are also used for detecting and measuring light over a wide wavelength range, which comprises the near infrared light, the visible light and the ultraviolet light of the electromagnetic spectrum.

Description of Related Art

A special rapid scanning spectrophotometer is known from U.S. Pat. No. 4,225,233, which produces illumination light with a predetermined wavelength depending on control voltage signals emitted to a scanning element. A scanning element, which in contrast to conventional spectrometers is arranged in the grating image plane of the spectrophotometer, is formed as a small mirror which is fixed to the rotor of a galvanometer. The angular position of said galvanometer is precisely controlled by a closed-loop electronic control circuit. The light spectrum reflected by the mirror is guided through a slit, thus providing light with the predetermined wavelength in a range of 50 to 300 nm or even 50 to 600 nm. The wavelength range is linearly scanned. A reduced wavelength precision must be accepted however in the higher wavelength range due to the limitation of the drive of the galvanometer.

In contrast to the generation of an illumination beam by a mirror for deflecting the spectrum provided by a monochromator for examining a sample, an order sorting filter (OSF) is provided downstream of the used dispersion grating in patent U.S. Pat. No. 7,924,422 B2 during the spectrometric detection of the light reflected from an examined object. This document discloses a calibration method for optical metrology. The illustrated OSF comprises three filtering zones, but it can also comprise fewer or more filtering zones. Each of the exemplary three filtering zones acts as a long-pass or bandpass filter in order to prevent that the pixels of the array detector (e.g. a CCD or CMOS sensor) situated directly beneath receive light of orders of diffraction which are higher than the measured orders of diffraction (typically one of the first orders +/−1). The disclosed OSF can be used for a wavelength range which reaches from near infrared light (NIR) via the visible light (VIS) and ultraviolet light (UV) up to deep ultraviolet light (DUV) of the electromagnetic spectrum. Order sorting filters with three zones are known from patent U.S. Pat. No. 7,924,422 B2, whose transmission range is produced by thin-film filter stacks which are all arranged on a common, optically transparent substrate and at least partly on bottom layers. The drawings show in FIG. 1A an order sorting filter with mutually abutting thin-film filter stacks (cf. FIG. 8 of U.S. Pat. No. 7,924,422 B2) and in FIG. 1B an order sorting filter with mutually partly overlapping thin-film filter stacks (cf. FIG. 9 of U.S. Pat. No. 7,924,422 B2).

Document U.S. Pat. No. 3,711,708 discloses a rapid scanner for detecting infrared spectrums at the output of a gas chromatograph, document EP 0 015 607 A1 discloses a modified Ebert monochromator for a spectrometer, and document WO 93/22636 A1 discloses a monochromator arranged on a separate housing and comprising one respective fixed inlet and outlet gap, a diffraction grating and an edge filter which is continuously driven by a grating drive and with angular synchronism in relation to the grating.

Document U.S. Pat. No. 6,313,471 B1 discloses a device for determining fluorescence, luminescence or absorption of a sample which is situated in a cuvette or in a well of a microplate. The device comprises a broadband light source, a monochromator arranged in a separate housing, and a filter wheel with a number of separate bandpass and/or edge filters for controlling the wavelength of the light impinging on the detector. The excitation light and the emission light are brought in one optical fibre each close to the sample in a well or close to the detector.

SUMMARY OF THE INVENTION

Microplate readers have long been known as optical measuring systems for detecting fluorescence, luminescence and/or absorption of samples in wells of a microplate and are available on the market in form of products of the current patent applicant for example. The microplate readers of the Infinite® family comprise apparatuses (monochromator, filter) for selecting specific wavelengths or rather wavelength ranges of the light for irradiating the samples in the microplate wells. The light arriving from the samples can also be subdivided by means of filters or a monochromator into preferred wavelength ranges and can be supplied to respective detectors.

All multi-well plates are designated as microplates within the scope of the present invention which comprise a plurality of wells or containers which are arranged in an array. Especially preferred microplates have at least the mass and the footprint of a microplate according to the SBS standard, as published by the American National Standards Institute (ANSI_SBS 1-2-3-4-2004). Microplates are known for example whose wells are equipped with a rounded bottom, a flat bottom or a V bottom. The wells can be arranged as "normal wells" or also as "deep wells".

Wells shaped in form of a truncated cone or truncated pyramid are generally known. It is a common feature of all microplates with different well shapes that they have a standardised base area, i.e. they have a standardised "footprint", and that the axial distance of the wells arranged in an array is also standardised. This axial spacing is, for example, 18 mm in 24 well (4×6) plates, 9 mm in 96-well (8×12) plates, 4.5 mm in 384 well (16×24) plates, and 2.25 mm in 1536 well (32×48) plates. The height of a microplate can vary greatly depending on the type and is typically between 10.4 mm (for example, 1536 V bottom deep well plate) and 44 mm (for example, 96 well Masterblock® from Greiner).

If the utilised wavelength range of a spectrometer extends over more than one octave, a certain fraction of light of half the wavelength is additionally admixed to the light of the set desired wavelength. Said fraction originates from the next higher order of diffraction of the grating, the undesirable light cannot be separated geometrically from the desired light (see FIG. 2). In order to retain said undesirable fractions from the wavelengths or wavelength ranges generated by a monochromator, spectral separation is known by the arrangement of long-pass filters (order sorting filters) in the light path. A respective filter must be used according to the selected wavelength. A long-pass filter with an edge wavelength of 350 nm is suitable, for example, in order to relieve the desired monochromator wavelengths in the range of approximately 360 nm to 680 nm from undesirable light of higher orders (less than 340 nm). If therefore a conventional spectrometer is to perform scanning over a wide wavelength range, several filter changes need to be performed. A scanning range of 200 nm to 1000 nm for example extends over more than two octaves and therefore requires three different long-pass filters, which leads to two changes of filters. Each change of the filter needs time, wherein it is also necessary to stop the movement of the monochromator grating. If it is intended to perform rapid scans with measurements over a wide wavelength range of 200 nm to 1000 nm, such interruptions caused by changing the filter are time-consuming and unacceptable.

It is an object of the present invention to provide a spectrometer for absorption spectrometry on samples in microplate wells, which comprises a combination of monochromator and order sorting filter, and which allows a continuous scan over a wavelength range of 200 nm to 1000 nm without having to stop the diffraction grating of the monochromator during scanning. This object is achieved by a spectrometer according to the features of independent claim 1.

It is an additional object of the present invention to provide a scanning method, in which a spectrometer with a combination of monochromator and order sorting filter is used in absorption spectrometry on samples in microplate wells during a rapid scan over a wavelength range of 200 nm to 1000 nm without stopping the diffraction grating of the monochromator during the scanning. This object is achieved by a scanning method according to the features of independent claim 17.

Further preferred and inventive features are provided in the respective dependent claims.

Advantages of the spectrometer in accordance with the invention, the order sorting filter in accordance with the invention, and the scanning method in accordance with the invention comprise the following:

The use of the order sorting filter which can be moved continuously and synchronously along with the diffraction grating of the monochromator allows the continuous detection of an absorption spectrum over a wavelength range of 200 nm to 1000 nm for example.

The detection of an absorption spectrum across a wavelength range of 200 nm to 1000 nm in steps of 1 nm requires less than five seconds.

The simple configuration of an order sorting filter for detecting an absorption spectrum across a wavelength range of 200 to 1000 nm, in which only two optically thin films of different characteristics concerning the spectral transmission are applied in an alternating manner to a quartz substrate, allows inexpensive production in comparison with conventional, linearly variable filters or seamlessly cemented filter combinations.

Four or more zones can be used for order sorting filters for detecting an absorption spectrum across an even broader wavelength range, wherein abutting zones are to be applied according to the same principle in an alternating fashion to the front and rear sides of the substrate.

The partial spatial overlapping of the two optically thin films reduces the requirements placed on the precision of the drive for the movement of the order sorting filter in comparison with a conventional seamlessly cemented filter combination.

The great distance between the two thin films on opposite sides of the substrate (approximately 1 mm thick) prevents interference and diffraction effects in the overlapping region, which occur in an order sorting filter with thin films situated on top of each other in the overlapping region on one substrate side (cf. U.S. Pat. No. 7,924,422 B2).

BRIEF DESCRIPTION OF THE DRAWINGS

An exemplary order sorting filter in accordance with the invention or rather an exemplary spectrometer in accordance with the invention are shown by way of schematic diagrams. These diagrams document selected embodiments of the subject matter of the invention, but do not limit the scope of the present invention, wherein.

DETAILED DESCRIPTION OF THE INVENTION

Examples of an order sorting filter in accordance with the invention and its use in a spectrometer or rather in performing a method in accordance with the invention will be explained below in closer detail. Reference is made especially to FIGS. 3 to 7A, because facts known from the prior art were already described by reference to FIGS. 1A, 1B and 2.

The same reference numerals in the drawings designate the same or at least similar features, even if they are not described in detail in each case.

Figure 1A:
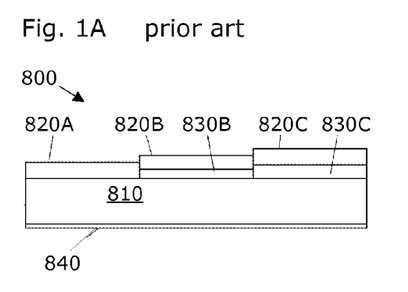
FIG. 1A shows an order sorting filter known from the state of the art, comprising three zones whose transmission range is produced by abutting thin-film filter stacks, which are all arranged on a common, optically transparent substrate and at least partly on bottom layers.

FIG. 1A shows an order sorting filter 800 known from the prior art, comprising three zones whose transmission range is produced by abutting thin-film filter stacks (cf. FIG. 8 of U.S. Pat. No. 7,924,422 B2).

The order sorting filter 800 comprises a substrate 810 which is common for all zones and a layer 840 which is arranged underneath, and thin-film filter stacks arranged above the substrate 810 for each zone. In the first zone, the thin-film filter stack only comprises a thin-film filter 820A, which is arranged directly on the substrate 810. In the second zone, the thin-film filter stack comprises a thin-film filter 820B and a bottom layer 830B, which is arranged between the thin-film filter 820B and the substrate 810. Similarly, the thin-film stack filter in the third zone comprises a thin-film filter 820C and a bottom layer 830C which is also arranged between the thin-film filter 820C and the substrate 810.

Figure 1B:
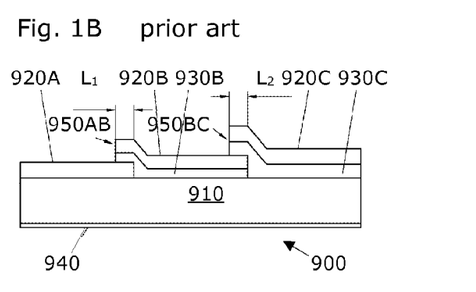
FIG. 1B shows an order sorting filter according to FIG. 1A with mutually partly overlapping thin-film filter stacks.

FIG. 1B shows an order sorting filter 900 known from the prior art and comprising three zones whose transmission range is produced by mutually partly overlapping thin-film filter stacks (cf. FIG. 9 of U.S. Pat. No. 7,924,422 B2). Similar to FIG. 8, the order sorting filter 900 comprises a substrate 910 with a layer 940 situated underneath and one thin-film filter stack per zone, which on their part comprise a thin-film filter 920A, a thin-film filter 920B with a bottom layer 930B, and a thin-film filter 920C with a bottom layer 930C.

The thin-film filter 920A lies directly on the substrate 910. The thin-film filter 920B lies mainly on the bottom layer 930B, however, in an overlapping region 950AB with a width L1 overlapping above the thin-film filter 920A of the first zone, such that in the overlapping region 950AB the following layer sequence from the bottom to the top results: the substrate 910, the thin-film filter 920A, the bottom layer 930B and the thin-film filter 920B. Similarly, the thin-film filter 920C lies mainly above the bottom layer 930C, however, in an overlapping region 950BC with a width L2 overlapping above the thin-film filter 920B of the second zone, such that the following layer sequence from the bottom to the top in the overlapping region 950BC results: substrate 910, bottom layer 930B, thin-film filter 920B, bottom layer 930C, and thin-film filter 920C.

Figure 2:
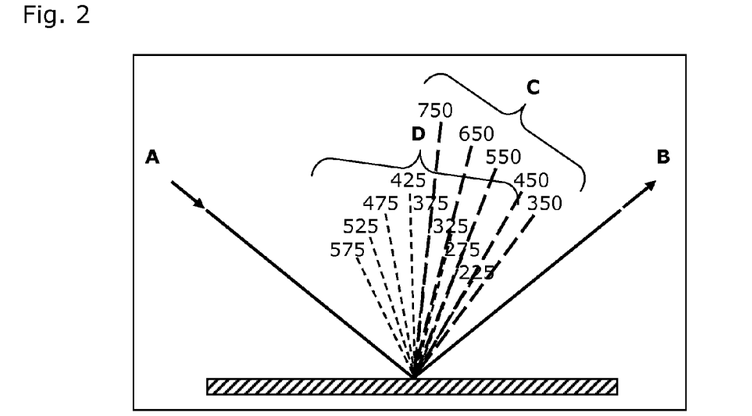
FIG. 2 shows a schematic view of orders of diffraction of the diffractive light known from the prior art, which is split by dispersion of the incident light on a diffraction grating of a monochromator.

FIG. 2 shows a schematic view of orders of diffraction of an incident light A known from the prior art, which light is split by means of diffraction on a diffraction grating. As a result of the diffraction grating (shown as a hatched beam), the incident light A is split into a first outgoing fraction B (unbroken line), a second outgoing fraction C (coarse dashed lines), and a third outgoing fraction D (fine dashed lines), wherein the various light beams are designated with a wavelength corresponding to the diffraction angle (the numbers correspond to the wavelength in nanometers). The first fraction B is designated as zero order of diffraction (zero order) and comprises all wavelengths of the incident light A. The second fraction C is designated as the first order of diffraction (first order) and comprises the light beams with the wavelengths of 350 nm, 450 nm, 550 nm, 650 nm and 750 nm. The third fraction D is designated as the second order of diffraction (second order) and comprises light beams with the wavelengths of 225 nm, 275 nm, 325 nm, 375 nm, 425 nm, 475 nm, 525 nm and 575 nm. It is obvious to the person skilled in the art that not only these special wavelengths are contained, respectively, but a continuum of wavelengths which are geometrically separated. The wavelength selection is thus achieved by applying a gap. The fraction C is desirable in a spectrometer, whereas the fraction D is undesirable.

Figure 3:
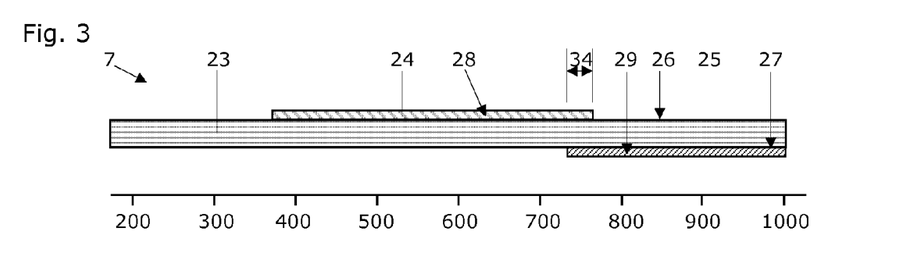
FIG. 3 shows a schematic longitudinal sectional view through an order sorting filter in accordance with the invention which is substantially rectangular and comprises three zones and long-pass filters formed rectangular and applied alternately.

FIG. 3 shows a schematic longitudinal sectional view through an order sorting filter 7 in accordance with the invention which is substantially rectangular and for which the abbreviation OSF is also used. The order sorting filter 7 comprises a substrate 23 with a first surface 26 and a second surface 27 opposite to the first surface 26. Rectangular optical thin films are arranged in an alternating fashion on the surfaces 26 and 27, namely a first optical thin film 24 on the first surface 26 and a second optical thin film 25 on the second surface 27. The optical thin films 24 and 25 are respectively arranged at a distance from a boundary region of the substrate 23, so that a section of the substrate 23 remains uncovered. Furthermore, the optical thin films 24 and 25 are offset with respect to each other along the surfaces 26 and 27, but are partly arranged mutually opposite to each other. The optical thin films are aligned in such a way that the edges of the optical thin films 24 and 25 are at least partly in alignment to the edges of the substrate 23, especially to the most part.

The term "optical thin film" designates a layer which typically consists of a series of alternating layers of nanometer thickness consisting of two or more different materials, e.g. of $TiO_2$ and $SiO_2$ layers which are arranged in an alternating fashion for example. These layers jointly produce the optical filtering effect.

The free boundary region of the substrate 23, i.e. the first section which is neither covered by the first optical thin film 24 nor by the second optical thin film 25, forms a first zone of the order sorting filter 7 and acts as a long-pass filter, e.g. with a long-pass edge wavelength in a range of approximately 160 nm to approximately 190 nm. The substrate 23 is made of a material such as glass or quartz for example which is transparent for visible light.

In a second section of the substrate 23, the first optical thin film 24 covers the substrate 23 on one side, i.e. the first optical thin film 24 is arranged on the first surface 26 of the substrate 23 and the second surface 27 of the substrate 23 remains uncovered. Said second section forms a second zone of the order sorting filter 7, which in this embodiment is a first long-pass filter 28 which has a long-pass edge wavelength in a range of approximately 300 to approximately 400 nm for example, especially of approximately 312 nm or approximately 375 nm.

In a third section of the substrate 23, the substrate 23 is covered on one side by the second optical thin film 25, i.e. the second optical thin film 25 is arranged on the second surface 27 of the substrate 23 and the first surface 26 of the substrate 23 remains uncovered. Said third section thus forms a third zone of the order sorting filter 7, which in this embodiment is a second long-pass filter 29 which has a long-pass edge wavelength in a range of approximately 400 nm to approximately 800 nm, especially of approximately 515 nm or approximately 740 nm.

A transitional region 34 is situated between the first and the second zones of the order sorting filter 7, which transitional zone is also referred as overlapping region, and which is formed by the covers on both sides by means of the two opposite optical thin films 24 and 25, i.e. by the first optical thin film 24 on the first surface 26 and the second optical thin film 25 on the second surface 27. In one example, the surface area of the transitional region 34 is less than 5% of the surface area of the substrate 23, especially less than 2%.

In a further example, the long-pass edge wavelength of the first optical thin film 24 is greater by a factor of between 1.5 and 2.5, especially by 1.9, than the long-pass edge wavelength of the substrate 23, and/or the long-pass edge wavelength of the second optical thin film 25 is greater by a factor of between 1.5 and 2.5, especially by 1.9, than the long-pass edge wavelength of the first optical thin film 24.

Sapphire crystal, $MgF_2$ glass, quartz glass, UV glass and float glass are understood for example as substrate materials with their respective edge positions or glass within the terms of the invention, as are known.

An exemplary order sorting filter 7 for a filter carriage 30 (cf. FIG. 5) has the following mass or properties:
Substrate: Quartz glass, thickness 1 mm, length 40 mm, width 7 mm;
$1^{st}$ long-pass filter 28: Length 12 mm, width 7 mm;
$2^{nd}$ long-pass filter 29: Length 6 mm, width 7 mm;
Spatial overlapping of the two long-pass filters 28, 29 by 1 mm at most, preferably 0.5 mm at most.

Figure 5:
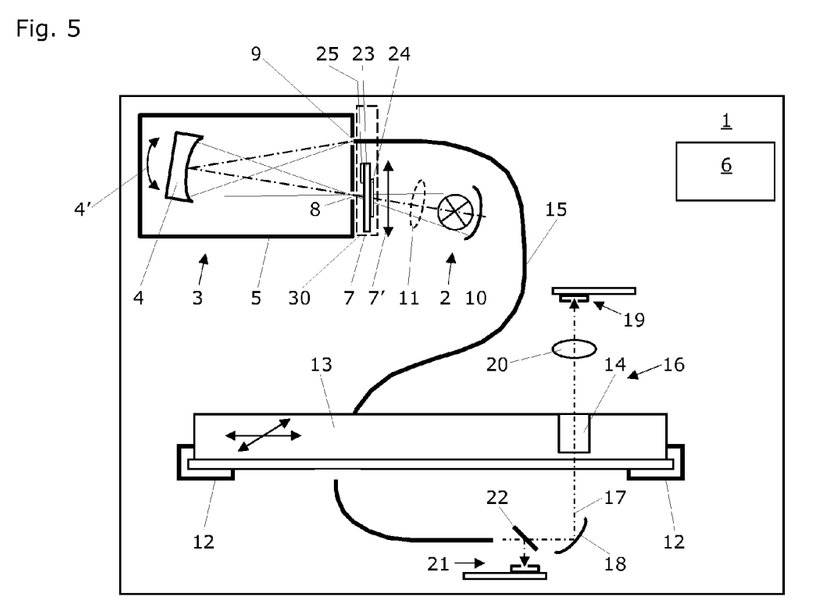
FIG. 5 shows a schematic vertical sectional view through a spectrometer in accordance with the invention, having a combination of monochromator and order sorting filter for the absorption spectrometry on samples in microplate wells.

In one embodiment, the order sorting filter 7 in accordance with the invention is used in a spectrometer, especially a spectrometer according to FIG. 5, and/or in a scanning method used to detect absorption spectrums of samples which are filled into wells 14 of microplates 13.

Figure 4:
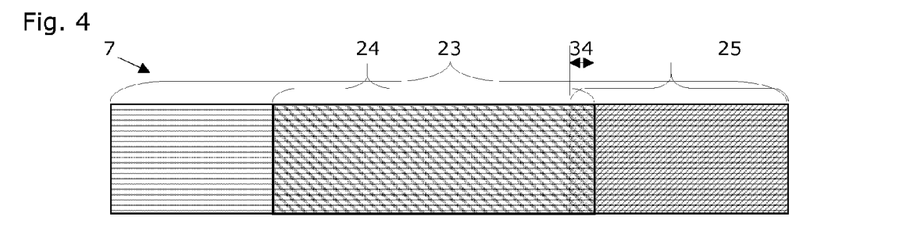
FIG. 4 shows a top view of an order sorting filter arranged according to FIG. 3.

FIG. 4 shows a top view of an order sorting filter 7 according to FIG. 3. The rectangular shape of the order sorting filter 7 is especially suitable for a linear or quasi-linear movement of the order sorting filter 7 in a spectrometer and/or monochromator.

FIG. 5 shows a schematic vertical sectional view through a spectrometer 1 in accordance with the invention for absorption spectrometry on samples in microplate wells. In this embodiment, the spectrometer 1 comprises a light source 2, a monochromator 3 with an order sorting filter 7, a microplate receptacle 12 with a microplate 13, a fibre-optic conductor 15, transmission optics 16 with a transmission axis 17 and a controller 6. The light source 2, which is provided in form of a flash lamp for example, comprises a condenser mirror 10 and a condenser lens 11, so that the light of the light source 2 can be conducted at least partly both directly as well as via the condenser mirror 10 to the condenser lens 11, and from said condenser lens 11 to the monochromator 3.

The monochromator 3 is operatively connected on the one hand to the light source 2, so that at least a part of the light generated by the light source 2 can be supplied to the monochromator 3, and on the other hand via the fibre-optic conductor 15 to the transmission optics 16, so that at least a portion of the exiting light of the monochromator 3 can be conducted to the transmission optics 16. The monochromator 3 comprises the order sorting filter 7, a diffraction grating 4 with a diffraction grating drive 4' and a monochromator housing 5 with an inlet gap 8 and an outlet gap 9. The order sorting filter 7 is arranged on a filter carriage 30 (shown with dashed line), so that the order sorting filter 7 is movable and can be displaced in a controlled manner by means of an order sorting filter drive 7' (shown by a double arrow). The diffraction grating 4 is mounted rotatable about a horizontal axis and is operatively connected to a diffraction grating drive 4', so that the diffraction grating 4 can be pivoted about the horizontal axis in a controlled manner (illustrated by a double arrow).

The order sorting filter 7 comprises a substrate 23 with a first surface 26 and a second surface 27 as well as a first optical thin film 24 and a second optical thin film 25. An order sorting filter 7 according to FIG. 3 is used in this example, so that the optical thin films 24 and 25 are arranged in an alternating manner with respect to the substrate 23 and are mutually offset to each other, but partly arranged opposite to each other in a transitional region 34. The uncovered substrate 23 forms the first zone, the first optical thin film 24 forms the second zone acting as the first long-pass filter 28, and the second optical thin film 25 forms the third zone acting as the second long-pass filter 29.

In another example, an order sorting filter known from the prior art is used, i.e. an order sorting filter with optical thin films applied on one side to the substrate, e.g. a conventional order sorting filter with a filter combination shown in FIG. 1A or 1B.

In the present embodiment, the order sorting filter 7 is arranged outside of the monochromator housing 5 and is in operative connection to the inlet gap 8 of the monochromator 3, so that the light exiting from the order sorting filter 7 is conducted through the inlet 8 to the diffraction grating 4 of the monochromator 3 and the order sorting filter 7 is thus provided upstream of the diffraction grating 4. The beam diameter of the light during the passage through the order sorting filter 7 is approximately 4 mm. The order sorting filter 7 can also be arranged at the outlet gap 9 of the monochromator 3, so that in this case the order sorting filter 7 is placed downstream of the monochromator 3.

The order sorting filter drive 4', e.g. a stepper motor, and the diffraction grating drive 4', which is also a stepper motor for example, are operatively connected to the controller 6, so that both the movement of the diffraction grating 4 as well as the movement of the order sorting filter 7 can be controlled by the controller 6. In accordance with the invention, the two drives 4' and 7' are controlled in a synchronised manner during the operation of the spectrometer 1, as will be described below in closer detail. The transmission optics 16 comprises a beam splitter 22, an elliptical deflection mirror 18, a measuring detector 19 with an upstream collecting lens 20 and a referencing detector 21.

The microplate receptacle 12 is adapted to accommodate the microplate 13, wherein the microplate 13 has e.g. a format according to the ANSI standard with a predetermined number of wells 14. The wells 14 are typically arranged in a large number (e.g. 96) of similar units in form of adjacent pocket hole bores in the microplates 13 (shown schematically as an individual well 14).

The housing 5 surrounds the monochromator 3 in a preferably virtually light-proof and dust-proof manner and is housed in the spectrometer 1 which is formed in this case as the microplate reader.

In this example, the measuring arrangement 19 is arranged on the transmission axis 17 of the transmission optics 16 and above the microplate 13, and the reference arrangement 21 is arranged on the transmission axis 17 and beneath the microplate 13. The transmission axis 17 is aligned in a substantially vertical way and penetrates the microplate 13 in the region of the wells 14 from the bottom side of the microplate receptacle 12 to the upper side of the microplate 13.

During the operation of the spectrometer 1, the light of the light source 2 (flash lamp) is supplied to the condenser lens 11 both directly as well as via reflexion on the condenser mirror 10, and is conducted from the condenser lens 11 via the order sorting filter 7 to the inlet gap 8 of the monochromator 3. In this process, the light is filtered according to the location of the passage by means of the order sorting filter 7, in that a respective short-wave fraction of the light is removed from the light according to the respectively passed zone or the transitional region 34. The filtered light is conducted from the inlet gap 8 to the diffraction grating 4 of the monochromator 3 and is diffracted there by means of the diffraction grating 4. A fraction of the diffracted light selected by the position of the diffraction grating 4 is then conducted as light of a defined wavelength to the outlet gap 9 of the monochromator 3.

The light passing through the outlet gap 9 is conducted by the fibre-optic conductor 15 to the transmission optics 16 and supplied to the beam splitter 22 of the transmission optics 16. The beam splitter 22 deflects a fraction of the incident light onto the referencing detector 21 on the one hand and conducts a further fraction of the incoming light to the elliptical deflection mirror 18 on the other hand. The elliptical deflection mirror 18 then guides the light received from the beam splitter 22 in the direction of the transmission axis 17 of the transmission optics 16, so that said light penetrates both the microplate 13 as well as the well 14 and the sample filled therein. The beam diameter of the light at the location of the sample is approximately 0.7 mm. The light coming from the well 14 is focused by means of the collecting lens 20 and is supplied to the measuring detector 19.

The measuring detector 19 detects the incoming light and transmits a respective electrical signal to an evaluation apparatus (not shown). Similarly, the referencing detector 21 detects the light impinging on the referencing detector 21 and transmits a respective electrical signal to the evaluation apparatus.

The evaluation apparatus, e.g. an electronic circuit and/or computer, evaluates the received electrical signals of the measuring detector 19 and the referencing detector 21 and produces a respective absorption spectrum of the sample arranged into the wells 14. The signal of the measuring detector 19 is normalised on the basis of the respective, synchronously detected signal of the referencing detector 21.

In accordance with the invention, the order sorting filter 7 and the diffraction grating 4 of the monochromator 3 are moved during the operation of the spectrometer 1 in a synchronous and continuous manner with each other by means of the controller 6. It is achieved as a result of this synchronisation that a respectively associated zone of the order sorting filter 7 is set in each of the respective angular positions of the diffraction grating 4, so that undesirable orders of diffractions are removed from the light of the monochromator 3.

The synchronisation in accordance with the invention is especially efficient because a continuous, i.e. interruption-free, synchronised movement of the diffraction grating 4 and the order sorting filter 7 is carried out. As a result, at the first order of diffraction, a passage of the light wavelengths (scan) across a spectrum of approximately 200 nm to approximately 1000 nm in steps of 1 nm is achieved in less than 5 seconds.

In this example, the movement of the order sorting filter 7 and the diffraction grating 4 occurs in a uniform manner, i.e. at constant velocity. In another example, the movement is carried out in a non-uniform manner, e.g. at a higher speed when passing the transitional region 34 than when passing other regions (zones) of the order sorting filter 7. In a further example, the long-pass edge wavelength of the order sorting filter 7 is assigned a wavelength of the diffraction grating 4 which is offset by a predetermined value (offset), e.g. by at least 10 nm, especially by at least 20 nm. For example, a first long-pass edge wavelength of 312 nm is assigned a diffraction grating wavelength of 350 nm and/or a second long-pass edge wavelength of 515 nm is assigned a diffraction grating wavelength of 550 nm.

Figure 6A:
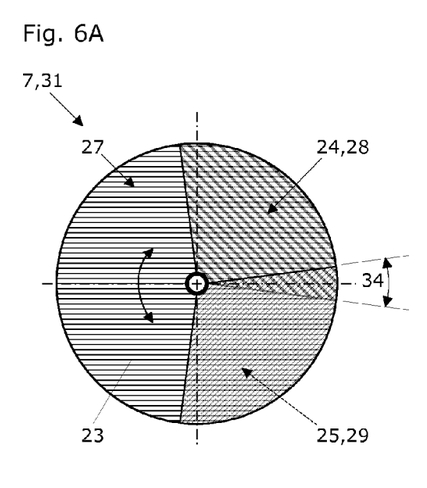
FIG. 6A shows a top view of an order sorting filter arranged in accordance with the invention as a rotatable filter disc and comprising sector-shaped long-pass filters applied alternately.

FIG. 6A shows a top view of an order sorting filter 7 in accordance with the invention, which is arranged as a rotatable filter disc 31. The filter disc 31 comprises a circular substrate 23 with a first surface and a second surface 27 which is opposite to the first surface. Similar to the rectangular order sorting filter 7 according to FIG. 3, sector-shaped optical thin films are arranged in an alternating fashion on said surfaces, namely a first optical thin film 24 on the first surface and a second optical thin film 25 on the second surface 27. The optical thin films 24 and 25 are angularly offset with respect to each other along the surfaces and are partly arranged opposite to each other with respect to the substrate 23 and leave a sector of the substrate 23 uncovered.

Accordingly, a first zone of the filter disc 31 is formed by the uncovered substrate 23, a second zone is formed by the unilateral covering by means of the first optical thin film 24, a third zone is formed by the unilateral covering by means of the second optical thin film 25, and a transitional region 34 is formed by the covering on both sides by means of the two optical thin films 24 and 25. The first zone forms a first long-pass filter 28 and the second zone forms a second long-pass filter 29.

An exemplary order sorting filter 7 in accordance with the invention for the filter disc 31 has the following sizes or rather properties:

Substrate: Thickness 1 mm, diameter 20 mm;
$1^{st}$ long-pass filter 28: Circular sector, diameter 20 mm, angle 180°;
$2^{nd}$ long-pass filter 29: Circular sector, diameter 20 mm, angle 90°;
Spatial overlapping of the two long-pass filters 28, 29 about an angle of 1° at most, preferably 0.5° at most.

Figure 6B:
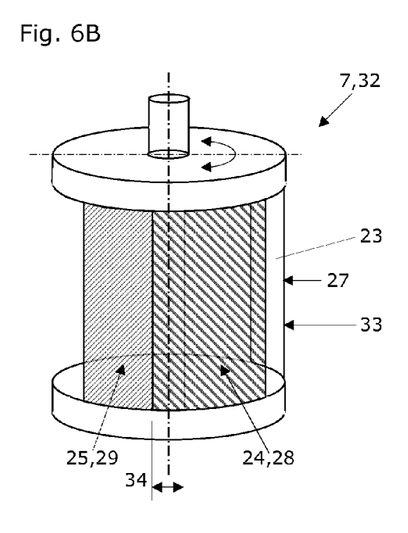
FIG. 6B shows a 3D view of an order sorting filter in accordance with the invention as a rotatable filter cylinder and comprising long-pass filters which are arranged as partial jacket surfaces and are applied alternately.

FIG. 6B shows a 3D view of an order sorting filter 7 in accordance with the invention, which is formed as a rotatable filter cylinder 32. The filter cylinder 32 comprises a half-side jacket surface 33 which forms a substrate 23 into the form of a partial jacket surface. The substrate 23 comprises an inner first surface as the inner wall and an outer second surface 27 as the outside wall. Optical thin films shaped in the form of partial jackets are arranged in an alternating fashion on the surfaces, similar to the rectangular order sorting filter 7 according to FIG. 3, namely a first optical thin film 24 on the first surface and a second optical thin film 25 on the second surface 27. The optical thin films 24 and 25 are offset with respect to each other along the surfaces of the substrate 23 and are partly arranged opposite to each other with respect to the substrate 23. Furthermore, a partial jacket surface of the substrate 23 is uncovered.

As in the preceding examples, a first zone of the order sorting filter 7 is formed by the uncovered substrate 23, a second zone is formed by the unilateral covering by means of the first optical thin film 24, a third zone is formed by the unilateral covering by means of the second optical thin film 25, and a transitional region 34 is formed by the covering on both sides by means of the two optical thin films 24 and 25. The first zone forms a first long-pass filter 28 and the second zone forms a second long-pass filter 29.

An exemplary order sorting filter 7 in accordance with the invention for the filter cylinder 32 has the following sizes or rather properties:

Substrate: Thickness 1 mm; as part of the jacket surface 33 with height 7 mm, diameter 26 mm, angle 180°;
$1^{st}$ long-pass filter 28: As part of the jacket surface 33 with height 7 mm, angle 90°;

2$^{nd}$ long-pass filter 29: As part of the jacket surface 33 with height 7 mm, angle 45°;

Spatial overlapping of the two long-pass filters 28, 29 about an angle of 1° at most, preferably 0.5° at most.

Figure 7A:
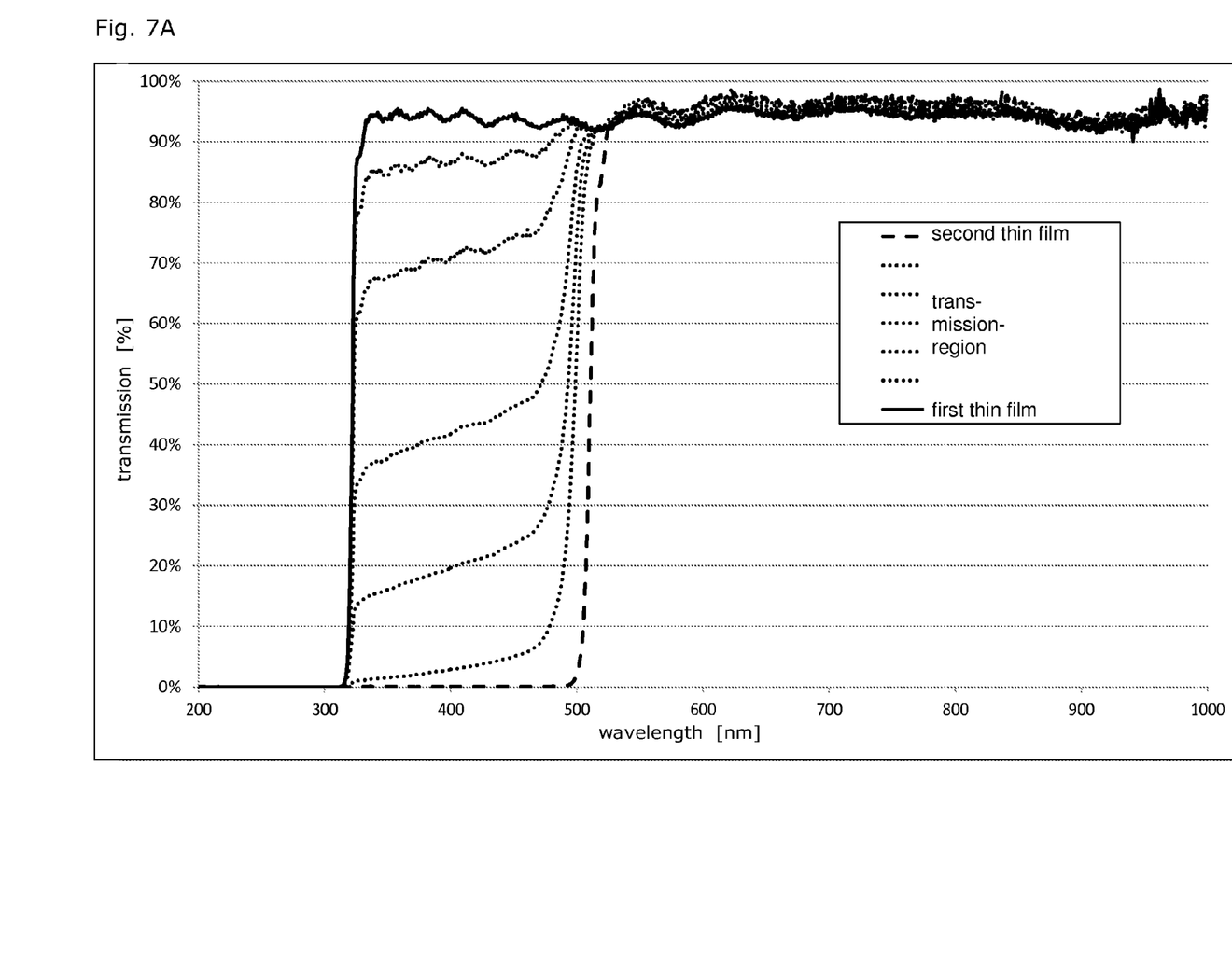
FIG. 7A shows a diagram in which the transmission of the first and second optical thin film and the overlapping region is shown depending on the wavelength and the position of the used light source, wherein the result of the measurement is shown on the basis of an order sorting filter in accordance with the invention with long-pass filters applied alternately.

FIG. 7A shows a diagram in which wavelength-dependent characteristic transmission curves are plotted at different light transfer positions in an order sorting filter in accordance with the invention. The wavelength-dependent characteristic transmission curves of the order sorting filter are shown at different light transfer positions through the order sorting filter: one position in the region of the single-layer first and second optical thin films (i.e. without overlapping) and 5 positions in the overlapping region of said optical thin films, respectively. The two optical thin films are arranged in an alternating fashion on the substrate, i.e. according to FIG. 3 for example the first optical thin film 24 on the first surface 26 of the substrate 23 and the second optical thin film 25 on the second surface 27 of the substrate 23 opposite surface with respect to the substrate 23.

The order sorting filter was arranged in different positions between a light source (flash lamp) and an entrance area of a fibre-optic conductor opposite to the light source during the measurement of the wavelength-dependent characteristic transmission curves. The wavelength-dependent characteristic transmission curve was respectively determined by means of a spectrometer arranged at the outlet of the fibre-optic conductor (HR4000 of Ocean Optics company, 830 Douglas Ave. Dunedin, Fla. 34698 USA). The order sorting filter was moved to different positions and plotting of the characteristic transmission curves was repeated. Consequently, the characteristic transmission curves were plotted at five different positions in the transitional region 34 (dotted lines) and a respective one in the two regions of the order sorting filter which are adjacent to the transitional region 34 and are covered on one side, i.e. at the first thin film (continuous line) and at the second thin film (dashed line). In this example, a filter was used having the optical thin films 24 and 25 applied by vapour deposition onto a quartz substrate (Item Number: LF102357) of DELTA company (Venlighedsvej 4, 2970 Hørsholm, Denmark).

Figure 7B:
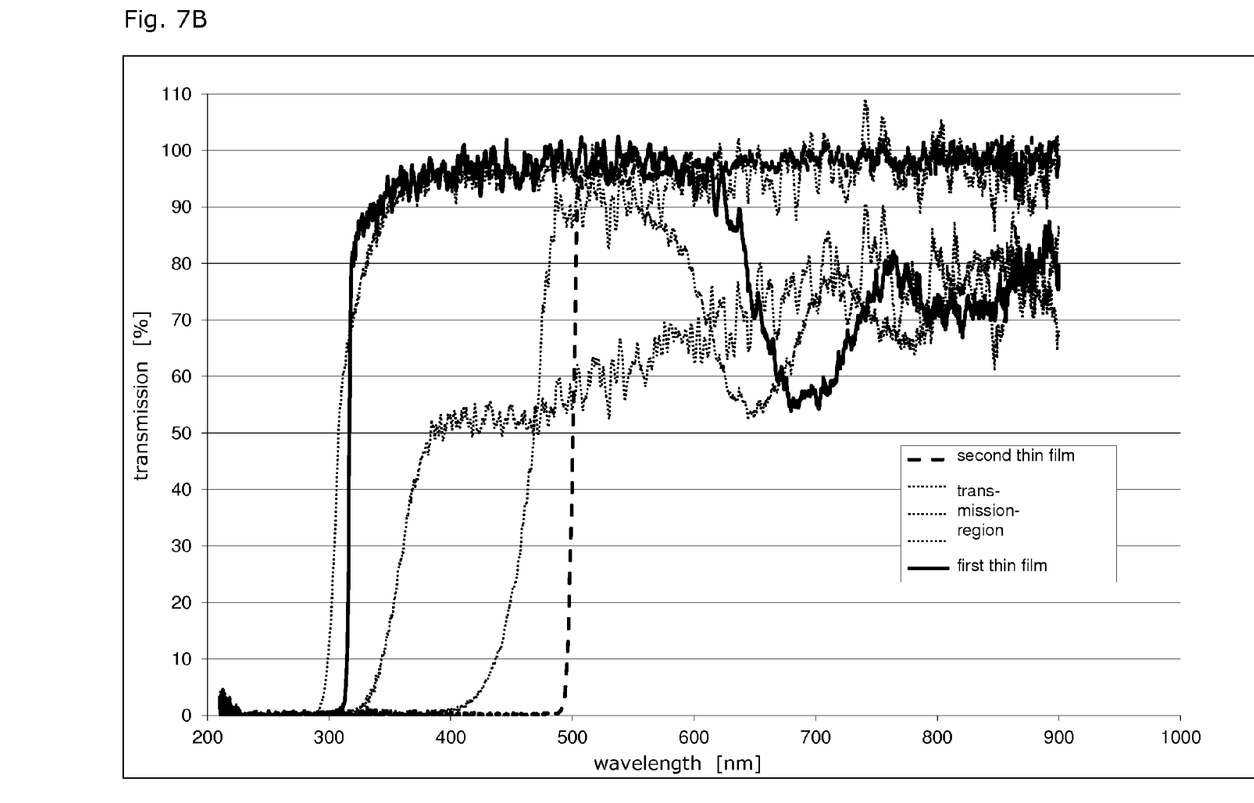
FIG. 7B shows a diagram according to FIG. 7A, wherein the result of the measurement is shown on the basis of an order sorting filter with long-pass filters applied to one side according to the prior art.

FIG. 7B shows a diagram concerning an order sorting filter as known from the prior art. The wavelength-dependent characteristic transmission curves of the order sorting filter are shown at different light transfer positions through the order sorting filter: one position in the region of the single-layer first and second optical thin films (i.e. without overlapping) and three positions in the overlapping region of these optical thin films, respectively. Further details to the measuring arrangement were already described in connection with FIG. 7A.

In contrast to the arrangement in accordance with the invention, the two optical thin films are arranged jointly and in an overlapping fashion on the one substrate side in the used conventional order sorting filter, e.g., according to FIG. 1B, on the upper surface of the substrate 910. Interference effects occur in the overlapping region of the two optical thin films (in FIG. 1B in the overlapping region 950AB or 950BC), so that the transmission in this transitional region 34 changes abruptly. Furthermore, the interference effects result to a reduced and highly fluctuating transmission in the passage region for long-wave light, i.e. in the case of wavelengths exceeding approximately 515 nm.

In the transitional region 34 or the intermediate region of the two optical thin films, a continuous increase in the transmission can be recognised during altering the measuring position from the first to the second optical thin film for the order sorting filter in accordance with the invention in FIG. 7A. Furthermore, the transmission is completely uninfluenced when passing through the thin films, in the transmission range for long-wave light, i.e. in case of wavelengths exceeding approximately 515 nm. Interference effects, as occur in FIG. 7B, are not present or only to an extent that cannot be determined. As a result of this continuous and substantially linear characteristic of the order sorting filter in accordance with the invention, a high quality of the measurements is achieved. The lack of the interference effects can be explained due to the separation of the two optical thin films by means of the substrate because the two optical thin films are arranged so far apart from each other by means of the substrate that they no longer influence each other.

A spectrometer 1 is thus proposed which comprises the following:

(a) a light source 2;
(b) a monochromator 3 with at least one diffraction grating 4;
(c) a monochromator housing 5;
(d) an order sorting filter 7 which is provided upstream or downstream of the diffraction grating 4 of the monochromator 3;
(e) a microplate receptacle 12, which is adapted to accommodate at least one microplate 13 which at least approximately has a format of microplates according to the ANSI standard and comprises a number of wells 14, and
(f) a controller (6), and which is characterized in that the order sorting filter 7 of said spectrometer 1 comprises a substrate 23, a first optical thin film 24 and a second optical thin film 25, wherein the first optical thin film 24 is arranged on a first surface 26 and the second optical thin film 25 is arranged on a second surface 27 of the substrate 23 in a spatially partly overlapping and interference-free manner.

The order sorting filter 7 and the diffraction grating 4 of the monochromator 3 preferably each comprise a drive 4', 7', which are operatively connected to the controller 6 of the spectrometer 1 in accordance with the invention in such a way that the order sorting filter 7 and the diffraction grating 4 of the monochromator 3 are continuously and synchronously movable with respect to each other.

In contrast to known filter solutions, e.g. conventional filter discs, linearly variable filters or gap-free cemented filter combinations, a short measuring time, a cost-effective configuration and high steadiness (low position sensitivity) are achieved by means of the order sorting filter in accordance with the invention.

The order sorting filter in accordance with the invention which shows the advantageous continuous transmission characteristic can be used in a large number of monochromators or in devices which are based on monochromators.

| List of reference numerals | | | |
|---|---|---|---|
| 1 | Spectrometer | 23 | Substrate |
| 2 | Light source | 24 | First optical thin film |
| 3 | Monochromator | 25 | Second optical thin film |
| 4 | Diffraction grating | 26 | First surface of 23 |
| 4' | Diffraction grating drive | 27 | Second surface of 23 |
| 5 | Monochromator housing | 28 | First long-pass filter |
| 6 | Controller | 29 | Second long-pass filter |
| 7 | Order sorting filter | 30 | Filter carriage |
| 7' | Order sorting filter drive | 31 | Filter disc |
| 8 | Inlet gap | 32 | Filter cylinder |
| 9 | Outlet gap | 33 | Jacket surface of 32 |
| 10 | Condenser mirror | 34 | Overlapping region, transitional region |
| 11 | Condenser lens | | |

-continued

| | List of reference numerals | | |
|---|---|---|---|
| 12 | Microplate receptacle | | |
| 13 | Microplate | | |
| 14 | Well | A | Incident light beam |
| 15 | Fibre-optic conductor | B | Reflected light of 0th order of diffraction (all wavelengths) |
| 16 | Transmission optics | | |
| 17 | Transmission axis | C | Reflected light of the first order of diffraction (desirable) |
| 18 | Deflection mirror | | |
| 19 | Measuring detector, measuring arrangement | D | Reflected light of second order of diffraction (undesirable) |
| 20 | Collecting lens | | |
| 21 | Referencing detector; reference arrangement | | |
| 22 | Beam splitter | | |

The invention claimed is:

1. A spectrometer (1), comprising
(a) a light source (2);
(b) a monochromator (3) with at least one diffraction grating (4);
(c) a monochromator housing (5);
(d) an order sorting filter (7), which is provided upstream or downstream of the diffraction grating (4) of the monochromator (3);
(e) a microplate receptacle (12) which is formed for accommodating at least one microplate (13) comprising one or more wells (14), and
(f) a controller (6),
characterized in that the order sorting filter (7) of said spectrometer (1) comprises a substrate (23), a first optical thin film (24), and a second optical thin film (25), wherein, in a spatially partly overlapping manner, the first optical thin film (24) is arranged on a first surface (26) of the substrate (23) and the second optical thin film (25) is arranged on a second surface (27) of the substrate (23);
wherein the first optical thin film (24) on the first surface (26) of the substrate (23) comprises a first long-pass filter (28) having a long-pass edge wavelength in a range of 300 to 400 nm, and the second optical thin film (25) on the second surface (27) of the substrate (23) is formed as a second long-pass filter (29) having a long-pass edge wavelength in a range of 400 to 800 nm.

2. The spectrometer (1) according to claim 1, characterized in that the order sorting filter (7) and the diffraction grating (4) of the monochromator (3) each comprise a drive (4', 7') which is operatively connected to the controller (6) in such a way that the order sorting filter (7) and the diffraction grating (4) of the monochromator (3) are continuously and synchronously movable with respect to each other.

3. The spectrometer (1) according to claim 1, wherein the monochromator housing (5) comprises an inlet gap (8) and an outlet gap (9), and wherein the spectrometer (1) is characterized in that the light source (2) being in operative connection with the inlet gap (8) and the order sorting filter (7) being in operative connection with the inlet gap (8) or with the outlet gap (9) are arranged outside the monochromator housing (5), respectively.

4. The spectrometer (1) according to claim 1, characterized in that the light source (2) functions as a flash lamp and comprises at least one of a condenser mirror (10) and a condenser lens (11).

5. The spectrometer (1) according to claim 1, characterized in that it comprises a fibre-optic conductor (15) which supplies the light of selected wavelengths, selected by means of the diffraction grating (4) of the monochromator (3) and relieved from undesirable orders of diffraction by means of the order sorting filter (7), to transmission optics (16) having a transmission axis (17).

6. The spectrometer (1) according to claim 5, characterized in that the transmission axis (17) is arranged substantially vertically and penetrates both the microplate receptacle (12) as well as an accommodated microplate (13) in the region of a well (14).

7. The spectrometer (1) according to claim 5, characterized in that the transmission optics (16) comprises an elliptical deflection mirror (18) for deflecting the light coming from the monochromator (3) in the direction of the transmission axis (17).

8. The spectrometer (1) according to claim 5, characterized in that the transmission optics (16) comprises a measuring detector (19) for detection and a collecting lens (20) provided upstream of the measuring detector (19) for focusing the transmission light arriving from a well (14) of the microplate (13).

9. The spectrometer (1) according to claim 5, characterized in that the transmission optics (16) comprises a referencing detector (21) for detection and a beam splitter (22) provided upstream of the referencing detector (21) for deflecting a fraction of the light arriving from the monochromator (3).

10. The spectrometer (1) according to claim 9, characterized in that the measuring assembly (19) of the transmission optics (16) is arranged on the transmission axis (17) above the microplate receptacle (12) and the accommodated microplate (13), and that the referencing detector (21) is arranged on the transmission axis (17) beneath the microplate receptacle (12) and the accommodated microplate (13).

11. The spectrometer (1) according to claim 1, characterized in that the substrate (23) is a glass plate having a long-pass edge wavelength of 160 to 190 nm.

12. The spectrometer (1) according to claim 11, characterized in that the first optical thin film (24) defines a long-pass edge wavelength which exceeds the long-pass edge wavelength of the substrate (23) by a factor of 1.9, and that the second optical thin film (25) defines a long-pass edge wavelength which exceeds the long-pass edge wavelength of the first optical thin film (24) by a factor of 1.9.

13. The spectrometer (1) according to claim 1, characterized in that the first optical thin film (24) on the first surface (26) of the substrate (23) is formed as a first long-pass filter (28) having a long-pass edge wavelength of 312 nm, and that the second optical thin film (25) on the second surface (27) of the substrate (23) is formed as a second long-pass filter (29) having a long-pass edge wavelength of 515 nm.

14. The spectrometer (1) according to claim 1, characterized in that the order sorting filter (7) is formed as a linear or quasi-linear movable filter carriage (30), wherein the substrate (23) of the order sorting filter (7) which is formed as a glass plate is formed in a substantially rectangular manner, and wherein the two long-pass filters (28, 29) also have a substantially rectangular shape.

15. The spectrometer (1) according to claim 1, characterized in that the order sorting filter (7) is formed as a rotatable filter disc (31), wherein the substrate (23) of the order sorting filter (7) which is formed as a glass plate is formed circularly, and wherein the two long-pass filters (28, 29) have a sector-shaped form.

16. The spectrometer (1) according to claim 1, characterized in that the order sorting filter (7) is formed as a rotatable filter cylinder (32) having a jacket surface (33), wherein the substrate (23) of the order sorting filter (7) which is formed as a glass plate is formed as a half of the jacket surface (33), and wherein the two long-pass filters (28, 29) mutually cover a respective portion of the glass plate.

17. The spectrometer (1) according to claim 1, wherein the microplate receptacle (12) is shaped for accommodating at least one microplate (13) which has a format according to the American National Standards Institute standards.

18. A scanning method for detecting absorption spectrum of a sample in a well (14) of a microplate (13), the method comprising:
providing the spectrometer (1) according to claim 1;
providing a microplate having wells in the microplate receptacle, and providing samples in one or more wells;
activating the light source to provide light, with the light from the light source being filtered by the order sorting filter, and also being diffracted by the diffraction grating;
wherein said filtered and diffracted light is directed to pass through a sample in a well of the microplate; and
detecting absorption signals for the sample.

19. The scanning method according to claim 18, characterized in that the order sorting filter (7) comprises overlapping regions (34) of the long-pass filter (28, 29) and is moved continuously and synchronously with the diffraction grating (4) of the monochromator (3) in such a way that each long-pass edge wavelength of an overlapping region (34) on the order sorting filter (7) is assigned a wavelength of the diffraction grating (4) of the monochromator (3), wherein a controller (6) of the spectrometer (1) synchronizes these movements with electronics of the measuring detector (19).

20. The scanning method according to claim 19, characterized in that a wavelength of the diffraction grating (4) of the monochromator (3) of 350 nm is assigned to a first long-pass edge wavelength of the order sorting filter (7) of 312 nm.

21. The scanning method according to claim 20, characterized in that a wavelength of the diffraction grating (4) of the monochromator (3) of 550 nm is assigned to a second long-pass edge wavelength of the order sorting filter (7) of 515 nm.

22. A scanning method according to claim 18, characterized in that:
a measuring detector (19) detects the absorption signals for the sample;
a referencing detector (21) detects reference signals; and
wherein said absorption signals are normalized according to respective synchronously detected reference signals.

* * * * *